(12) United States Patent
Torrence

(10) Patent No.: US 7,423,064 B2
(45) Date of Patent: Sep. 9, 2008

(54) COMPOSITION FOR TREATING BACTERIAL, VIRAL, FUNGAL DISEASES, INFLAMMATION AND PAIN

(75) Inventor: Christopher Torrence, Darien, CT (US)

(73) Assignee: Olatec Industries, LLC, Rye Brook, NY (US)

( * ) Notice: Subject to any disclaimer, the term of this patent is extended or adjusted under 35 U.S.C. 154(b) by 112 days.

(21) Appl. No.: 11/234,874

(22) Filed: Sep. 23, 2005

(65) Prior Publication Data

US 2006/0069160 A1 Mar. 30, 2006

Related U.S. Application Data

(60) Provisional application No. 60/714,509, filed on Sep. 24, 2004.

(51) Int. Cl.
*A01N 37/44* (2006.01)
(52) U.S. Cl. .................................................. 514/562
(58) Field of Classification Search .................. 514/562
See application file for complete search history.

(56) References Cited

U.S. PATENT DOCUMENTS

| | | | |
|---|---|---|---|
| 3,776,825 A | 12/1973 | Vit | |
| 3,943,628 A | 3/1976 | Kronman et al. | |
| 3,991,107 A | 11/1976 | Vit | |
| 4,012,842 A | 3/1977 | Vit | |
| 4,314,989 A | 2/1982 | Rosen | |
| 4,386,103 A | 5/1983 | Pogany et al. | |
| 4,902,718 A | 2/1990 | Bayless et al. | |
| 4,927,850 A | 5/1990 | Bayless et al. | |
| 5,053,429 A | 10/1991 | Hirsch et al. | |
| 5,084,482 A | 1/1992 | Hirsch et al. | |
| 5,430,064 A | 7/1995 | Hirsch et al. | |
| 5,703,127 A | 12/1997 | Pak | |
| 5,712,311 A | 1/1998 | Soudant et al. | |
| 5,715,835 A | 2/1998 | Lishko et al. | |
| 5,853,768 A | 12/1998 | Altadonna | |
| 5,952,367 A | 9/1999 | Pak | |
| 6,193,956 B1 | 2/2001 | Liu et al. | |
| 6,419,913 B1 | 7/2002 | Niemiec et al. | |
| 6,451,761 B1 | 9/2002 | Gelder et al. | |
| 6,482,401 B1 | 11/2002 | Knigge | |
| 6,593,331 B2 | 7/2003 | Camborde et al. | |
| 6,689,399 B1 | 2/2004 | Dickson | |

OTHER PUBLICATIONS

Armesto et al. First steps in the oxidation of sulfur-containing amino acids by hypohalogenation: very fast generation of intermediate sulfenyl halides and halosulfonium cations. Tetrahedron 56 (2000) 1103-1109.*
PCT/US06/10665, International Search Report, Aug. 1, 2006.
Matthew B. Grisham, et al., "Chlorination of Endogenous Amines by Isolated Neutrophils", The Journal of Biological Chemistry, vol. 259, No. 16, Issue of Aug. 25, pp. 10404-10413 (1984).
Alexander V. Peskin, et al., "Kinetics of the Reactions of Hypochlorous Acid and Amino Acid Chloramines with Thiols, Methionine, and Ascorbate", Free Radical Biology & Medicine, vol. 30, No. 5, pp. 572-579 (2001).
Grazyna Drabik, et al., "Chlorination of N-acetyltyrosine with HOCl, chloramines, and myeloperoxidase-hydrogen peroxide-chloride system", Acta Biochimica Polonica, vol. 48 No. 1 (2001).

* cited by examiner

*Primary Examiner*—Sreeni Padmanabhan
*Assistant Examiner*—Renee Claytor
(74) *Attorney, Agent, or Firm*—Howrey LLP; Viola T. Kung

(57) ABSTRACT

The present invention is directed to compositions and methods of treating bacterial, viral, fungal diseases; inflammation or inflammatory-related disorders; pain; and skin conditions. The composition comprises an organic solvent extract, which is prepared by the method comprising the steps of: (a) mixing methionine with water, (b) adding an aqueous hypochlorite solution to the methionine solution and mixing, (c) adding a water-immiscible organic solvent to (b) and mixing, and (d) separating the organic solvent phase from the water phase to obtain the organic solvent extract.

11 Claims, No Drawings

COMPOSITION FOR TREATING BACTERIAL, VIRAL, FUNGAL DISEASES, INFLAMMATION AND PAIN

This application claims the benefit of U.S. Provisional Application No. 60/714,509, filed Sep. 24, 2004.

FIELD OF THE INVENTION

The present invention relates to compositions and methods of treating bacterial, viral, fungal diseases; inflammation or inflammatory-related disorders; pain; and skin conditions. The composition is prepared by the organic solvent extraction of a reaction product of methionine and hypochorite.

BACKGROUND OF THE INVENTION

The human body is susceptible to many different types of infections from a variety of sources. Viral infection, usually in the form of the common cold, affects virtually everyone each year. While the coughing and sneezing associated with colds may be merely annoying, other common viral infections can be far more serious. Influenza, for example, remains a leading cause of hospitalization and death among Americans, accounting for an average of 36,000 fatalities and 114,000 hospitalizations per year.

Bacterial infections can be just as dangerous. *Staphylococcus* infections, which are caused by bacteria from the *staphylococcus* family, account for many serious post-surgical complications. *Staphylococcus* infection is also the leading culprit in cases of food poisoning, and can be responsible for such life-threatening conditions as Toxic Shock Syndrome (TSS), pneumonia, bone infections (osteomyelitis), mastitis in nursing mothers, endocarditis (infection of the inside of the heart), and bacteremia (blood infection). People who are otherwise healthy typically do not become severely ill from *staphylococcus* infections, but individuals with weakened immune systems, including the elderly, newborns, and persons with chronic illnesses, such as diabetes, cancer, lung disease, kidney disease, or HIV/AIDS, are at special risk.

Individuals with weakened immune systems are at risk from fungal infections. Fungal infections cause conditions in millions of people in the form of sinus infections, athlete's foot, and yeast infections.

The general term "pain" used herein represents all categories of pain, such as traumatic pain resulting from injury, post surgical pain, inflammatory pain; pain associated with disease such as cancer, AIDS, arthritis, herpes, migraine; pain associated with neuropathy such as diabetic neuropathy, causalgia, brachial plexus avulsion, occipital neuralgia, fibromyalgia, gout, and other forms of neuralgic, neuropathic and idiopathic pain syndromes; pain of varying severity, i.e. mild, moderate and severe pain; acute and chronic pain; and specific organ pain, such as ocular and corneal pain, bone pain, heart pain, skin/burn pain, visceral (kidney, gall bladder, etc.), joint, dental and muscle pain.

Connective tissues are subjected to a constant barrage of stress and injury. Acute or chronic impacts and the natural progression of various degenerative diseases all produce painful inflammation in joint regions, such as the neck, back, arms, hips, ankles and feet. These afflictions are common and often debilitating.

Current therapies of pain include the use of opiod narcotic analgesics such as morphine and fentanyl, nonsteroidal anti-inflammatory drugs (NSAIDS) such as aspirin, ibuprofen and cyclooxygenase inhibitors, or ion channel blockers such as lidocaine and novacaine. These therapies all have limitations, for example, they cause tolerance, dependence, constipation, respiratory depression and sedation (opiods). NSAIDS have gastrointestinal side effects and increase bleeding time, and are not effective in treating severe pain.

Inflammation is a localized reaction of live tissue due to an injury, which may be caused by various endogenous and exogenous factors. The exogenous factors include physical, chemical, and biological factors. The endogenous factors include inflammatory mediators, antigens, and antibodies. Endogenous factors often develop under the influence of an exogenous damage. An inflammatory reaction is often followed by an altered structure and penetrability of the cellular membrane. At the tissue and organ level, inflammation is indicated by pain, swelling, reddening, increased temperature, and loss of function in some cases.

Inflammation is influenced by various exogenous and endogenous agents. Endogenous factors, namely, mediators, antigens, and autogens define the nature and type of an inflammatory reaction, especially its course in the zone of injury. In the case where a tissue damage is limited to the creation of mediators, an acute form of inflammation develops. If immunologic reactions are also involved in the process, through the interaction of antigens, antibodies, and autoantigens, a long-term inflammatory process will develop. Various exogenous agents, for example, infection, injury, radiation, also provide the course of inflammatory process on a molecular level by damaging cellular membranes which initiate biochemical reactions.

Nonsteroidal anti-inflammatory drugs (NSAIDS), such as aspirin, can block certain links of an inflammatory process, but these drugs cannot stabilize damaged cellular membranes, which makes their influence on an inflammatory process limited and insufficient.

There is a need for a composition and a method for treating bacterial, viral, fungal diseases; inflammation or inflammatory-related disorders; pain; and skin conditions. The composition should be economic and easy to manufacture, and the method should be effective and have no significant side effects.

SUMMARY OF THE INVENTION

The present invention is directed to an organic solvent extract prepared by the reaction of an aqueous methionine solution with an aqueous hypochlorite solution, and the extraction of the reactive product with a water-immiscible organic solvent such as mineral oil. The reactive product is stable in the water-immiscible organic solvent for at least several months at room temperature.

The present invention is also directed to a method for treating bacterial, viral, fungal diseases; inflammation or inflammatory-related disorders; pain; or skin conditions. The method comprises the step of administering to a subject in need thereof a composition comprising the organic solvent extract as prepared according to the present invention. The composition can be applied by any of the accepted modes of systemic administration including topical, oral, and parenteral (such as intravenous, intramuscular, subcutaneous or rectal). Topical administration and oral administration are preferred.

DETAILED DESCRIPTION OF THE INVENTION

The present invention describes an organic solvent extract that is useful in treating a variety of diseases or disorders. The organic solvent extract is prepared by the method comprising the steps of: (a) mixing methionine with water, (b) adding an aqueous hypochlorite solution to the methionine solution and mixing at a temperature between 0° C. to ambient temperature, (c) adding a water-immiscible organic solvent to (b) and mixing, and (d) separating the organic solvent phase from the water phase to obtain the organic solvent extract.

The organic solvent extract is prepared by first preparing a reactive product, and then stabilizing the reactive product by extracting it into a water-immiscible organic solvent.

The reactive product is prepared by first mixing methionine with water until a suspension is formed. Methionine can be L-methionine, D-methionine, or a mixture thereof. The mixing is preferably carried out under an inert gas, e.g. argon. The mixing time is typically a few seconds to a few minutes. The mixing can be done by any means of mixing, for example, by a blender.

An aqueous solution of hypochlorite such as sodium hypochlorite is added to the methionine solution and thoroughly mixed. Then the reaction mixture is rested until the mixture is cleared and the excess methionine forms foam on the top. The foam is optionally removed. The reaction is carried out at a temperature between 0° C. to ambient temperature, preferably at a low temperature such as 0-5° C. The reaction is preferably carried out under an inert gas such as argon.

The reactive product is not stable in water and is extracted with a water-immiscible organic solvent. The water-immiscible organic solvent useful is this invention is preferably a semi-polar or non-polar solvent having a polarity of about 0.1-7.5, such as mineral oil, hexane, heptane, methylene chloride, vegetable oil, or ethyl acetate. A non-polar solvent is more preferred. The extraction is carried out immediately after the methionine/hypochlorite reaction, preferably, within 5 minutes, preferably within 2 minutes, and more preferably within 1 minute.

The water-organic solvent mixture is allowed to settle. The organic phase is separated from the water phase by any means known to a skilled person such as pouring or pipetting, and the organic solvent extract is obtained. Any non-soluble residues in the organic solvent extract are optionally removed by filtration, decanting, centrifugation, or any means known to a skilled person. The reactive product is stable in the organic solvent at room temperature (22-28 ° C.) for at least a month, preferably, 3 months, more preferably 6 months or a year.

In a typical reaction, 700-800 ml of distilled water, 20-100 g of methionine, and 300-500 ml of 3-12% hypochlorite are used. In a typical extraction, about 200-300 ml or more water-immiscible organic solvent is used. The amounts of the above reagents can be scaled up or scaled down.

The organic solvent extract of the present invention is useful for treating a variety of diseases or disorders. The organic solvent extract can be used as is, or it can be administered in the form of a pharmaceutical composition that additionally contains a pharmaceutically acceptable carrier. In one embodiment, the organic solvent extract can be incorporated into any acceptable carrier, including creams, gels, lotions or other types of suspensions that can stabilize the active ingredient and deliver it to the affected area by topical applications. In another embodiment, the pharmaceutical composition can be in the dosage forms such as tablets, capsules, granules, fine granules, powders, syrups, suppositories, injections, or the like. The above pharmaceutical composition can be prepared by conventional methods.

In one embodiment, the present invention provides a method of treating a bacterial disease such as *staphylococcus* infection.

In another embodiment, the present invention provides a method of treating a viral disease such as influenza infection.

In another embodiment, the present invention provides a method of treating a fungal disease such as athlete's foot, yeast infection, and sinus infection caused by fungus infection.

In another embodiment, the present invention provides a method of treating a skin condition such as skin damages by burns or sun, skin blotches, or wart.

In another embodiment, the present invention provides a method of treating inflammation or inflammatory-related disorders. The present invention alleviates symptoms associated with inflammation or inflammatory-related disorders, such as pain, swelling, reddening, increased temperature, or loss of function in some cases.

In yet another embodiment, the present invention provides a method to alleviate the symptoms of pain regardless of the cause of the pain. The general term "pain" treatable by the present method includes traumatic pain, neuropathic pain, organ pain, and pain associated with diseases. Traumatic pain includes pain resulting from injury, post-surgical pain and inflammatory pain. Neuropathic pain includes neuropathic and idiopathic pain syndromes, and pain associated with neuropathy such as diabetic neuropathy, causalgia, brachial plexus avulsion, occipital neuralgia, fibromyalgia, gout, and other forms of neuralgia. Organ pain includes ocular, corneal, bone, heart, skin/burn, visceral (kidney, gall bladder, etc.), joint, dental and muscle pain. Pain associated with diseases includes pain associated with cancer, AIDS, arthritis, herpes and migraine. The present invention reduces pain of varying severity, i.e. mild, moderate and severe pain; acute and chronic pain. For example, the present invention is effective in treating pain derived from inflammatory arthritis or degenerative arthritis, joint pain, muscle pain, tendon pain, and burn pain.

The methods of the present invention comprises the step of administering to a subject in need thereof a composition comprising the organic solvent extract as prepared according to the present invention. The composition of the present invention can be applied by any of the accepted modes of systemic administration including topical, oral, parenteral (such as intravenous, intramuscular, subcutaneous or rectal), and otherwise systemic routes of administration. Dosing of the composition can vary based on the extent of the injury and each patient's individual response. Topical administration and oral administration are preferred.

When applied topically, the composition is preferably applied onto the affected area and rubbed into it. The composition can be applied 1-5 times daily, preferably 1-3 times daily, and preferably 3 times daily. The active compound passes through the skin and is delivered to the site of discomfort. Those of skill in the art will recognize that a wide variety of delivery mechanisms other than topical application, e.g., ingestible tablets, ingestible liquids, inhalers and aerosols are also suitable.

The following examples further illustrate the present invention. These examples are intended merely to be illustrative of the present invention and are not to be construed as being limiting.

EXAMPLES

Example 1

Preparation of Product

In a blender, 720-750 ml of distilled water at 0-4° C. and 20 g DL methionine fine powder (Degussa Corp., Richfield Park, N.J.) were combined and mixed for a few seconds under argon. After the methionine solid is uniformly suspended in the distilled water, 370-400 ml of Clorox bleach (6% sodium hypochlorite) at 0-4° C. was added and mixed at a blend speed for 30 second under argon. The reaction was rested for 30 seconds to a minute until the solution was cleared and the foam formed on top. The foam was excess methionine and was optionally removed.

The solution was immediately (<2 minutes) poured into an extraction blender and added with 240 ml of mineral oil (STO Oil Corp., San Marcos, Tex.) at room temperature, then blended at low speed for 20 seconds under argon.

The water-oil mixture was allowed to settle for 3-4 hours, and then the oil phase was removed and filtered through 20-micron filter paper. The filtrate was stored in an open container for 3 days to allow argon to dissipate, and the oil filtrate was ready to be used as a product.

Example 2

Hepatotoxicity Trials

An in vivo evaluation for hepatotoxicity of the product of Example 1 was performed on a rat population.

A control group of ten rats were untreated for control analysis of baseline serum enzymes and histology.

A second group of ten rats were gavaged twice daily with a standard saline solution to gauge the effects of repeating handling and gavaging on the liver.

A third group of twenty-five rats were gavaged twice daily with mineral oil alone.

A fourth group of twenty-five rats were gavaged twice daily with the product of Example 1.

After 28 days, the rats were anesthetized and their livers were tested according to standard methodology. It was concluded that consumption of the product of Example 1 did not result in any signs of hepatotoxicity.

Example 3

Treatment of Infections

The product of Example 1 was used to treat subjects who exhibited various infections. The results are summarized in Table 1.

TABLE 1

| Subject | Condition | Method of Application | Application | Results |
|---------|-----------|----------------------|-------------|---------|
| Subject 1 | Staphylococcal infection of leg | Topical | 3 months | Symptoms relieved |
| Subject 2 | Sinus condition | Topical | 1 week | Symptoms relieved |

Example 4

Treatment of Joint and Muscle Pain

Subjects having joint pain, bug bite pain, or burn pain were treated with the product of Example 1. The results are summarized in Table 2.

TABLE 2

| Subject | Condition | Method of Application | Relief Time |
|---------|-----------|----------------------|-------------|
| Subject 1 | Hip joint pain | Topical | Immediate |
| Subject 3 | Arthritic pain | Topical | Immediate |
| Subject 4 | Back/knee pain | Topical | Immediate |
| Subject 5 | Knee pain | Topical | Immediate |
| Subject 6 | Back/knee pain | Topical | Immediate |
| Subject 7 | Hip pain | Topical | Immediate |
| Subject 8 | Arthritic hand | Topical | Immediate |
| Subject 2 | Hand burn pain | Topical | Immediate |
| Subject 1 | Bug bite pain | Topical | Immediate |

Table 2 shows that subjects with various pain, when applied with the product topically, resulted in immediate relief of the pain.

Example 5

Treatment of Wounds or Injuries

The product of Example 1 was applied to individuals having burns or skin conditions topically three times a day as indicated in Table 3. After application of the product, the symptoms of the subjects were relieved.

TABLE 3

| Subject | Condition | Method of Application | Application Time |
|---------|-----------|----------------------|------------------|
| Subject 1 | Burns | Topical | 3 days |
| Subject 9 | Sun face blotches | Topical | 3 months |
| Subject 10 | Purple sun burn | Topical | 3 days |
| Subject 11 | Sun damage to skin | Topical | 2 months |
| Subject 12 | Sun damage to skin | Topical | 2 months |
| Subject 13 | Bleeding facial skin | Topical | 2 weeks |
| Subject 2 | Wart | Topical | 3 weeks |
| Subject 14 | Diabetic sores of legs and feet | Topical | 1 week |

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude the specification.

What is claimed is:

1. An organic solvent extract prepared by the method comprising the steps of:
    (a) mixing methionine with water,
    (b) adding an aqueous hypochlorite solution to (a) and mixing at a temperature between 0° C. to ambient temperature,
    (c) adding a water-immiscible organic solvent to (b) and mixing, and
    (d) separating the organic solvent phase, wherein step (c) is carried out within 5 minutes after step (b).

2. The organic solvent extract according to claim 1, wherein said water-immiscible organic solvent is hexane, heptane, methylene chloride, mineral oil, vegetable oil, or ethyl acetate.

3. The organic solvent extract according to claim 2, wherein said water-immiscible organic solvent is mineral oil or hexane.

4. The organic solvent extract according to claim 1, wherein the steps (a) and (b) are carried out under inert gas.

5. The organic solvent extract according to claim 1, wherein the methionine is D-methionine, L-methionine, or a mixture thereof.

6. A method of treating pain in a subject comprising the step of administering a composition comprising the organic solvent extract of claim 1 to a subject suffering from pain and wherein said pain is joint pain or burn pain.

7. The organic solvent extract according to claim 1, wherein the water-immiscible organic solvent is a non-polar organic solvent.

8. The organic solvent extract according to claim 3, wherein the water-immiscible organic solvent is mineral oil.

9. The organic solvent extract according to claim 1, further comprising the step of removing non-soluble residues after separating the organic solvent phase.

10. The organic solvent extract according to claim 9, wherein the non-soluble residues is removed by filtration, decanting, or centrifugation.

11. The organic solvent extract according to claim 1, wherein the mixing in step (b) is at a temperature between 0° C. to 5° C.

* * * * *